(12) United States Patent
Estevez et al.

(10) Patent No.: US 10,905,434 B2
(45) Date of Patent: Feb. 2, 2021

(54) RELOADABLE AND ROTATABLE CLIP

(71) Applicant: BOSTON SCIENTIFIC SCIMED, INC., Maple Grove, MN (US)

(72) Inventors: Ramon Estevez, Lowell, MA (US); Naroun Suon, Lawrence, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 297 days.

(21) Appl. No.: 16/116,731

(22) Filed: Aug. 29, 2018

(65) Prior Publication Data
US 2019/0090882 A1 Mar. 28, 2019

Related U.S. Application Data

(60) Provisional application No. 62/564,805, filed on Sep. 28, 2017.

(51) Int. Cl.
*A61B 17/128* (2006.01)
*A61B 17/122* (2006.01)
*A61B 17/00* (2006.01)
*A61B 17/12* (2006.01)
(Continued)

(52) U.S. Cl.
CPC ...... *A61B 17/1285* (2013.01); *A61B 17/0057* (2013.01); *A61B 17/1222* (2013.01); *A61B 17/1227* (2013.01); *A61B 90/03* (2016.02); *A61B 2017/0034* (2013.01);
(Continued)

(58) Field of Classification Search
CPC .............. A61B 17/122; A61B 17/1222; A61B 17/1227; A61B 17/128; A61B 17/1285; A61B 2017/00584; A61B 2090/037
See application file for complete search history.

(56) References Cited

U.S. PATENT DOCUMENTS 7,452,327 B2 * 11/2008 Durgin ............... A61B 17/1285
600/104
7,494,461 B2 * 2/2009 Wells ................... A61B 17/122
600/104
(Continued)

FOREIGN PATENT DOCUMENTS

EP 1829489 9/2007
EP 1882451 1/2008
(Continued)

*Primary Examiner* — Ryan J. Severson
(74) *Attorney, Agent, or Firm* — Fay Kaplun & Marcin, LLP (57) ABSTRACT

A system for treating tissue includes a clip assembly having a pair of clip arms. Proximal ends of the clip arms engage a distal portion of a central member slidably received within a channel of a capsule to be moved between an open configuration and a closed configuration. The central member includes the distal portion and a proximal portion connected to one another via a releasable connection which releases when subject to a force exceeding a predetermined threshold level. The system also includes an applicator releasably coupled to the clip assembly. The applicator includes an outer sleeve through which a control member extends. A distal end of the control member engages a cavity of the proximal portion to move the central member relative to the capsule. A lumen of the outer sleeve is sized and shaped to slidably receive the capsule therein.

20 Claims, 7 Drawing Sheets

(51) Int. Cl.
*A61B 90/00* (2016.01)
*A61B 17/29* (2006.01)

(52) U.S. Cl.
CPC ............. *A61B 2017/00584* (2013.01); *A61B 2017/12004* (2013.01); *A61B 2017/2929* (2013.01); *A61B 2090/037* (2016.02)

(56) References Cited

U.S. PATENT DOCUMENTS

| | | | | |
|---|---|---|---|---|
| 8,083,668 | B2* | 12/2011 | Durgin | A61B 34/76 600/104 |
| 8,162,959 | B2* | 4/2012 | Cohen | A61B 17/122 606/142 |
| 8,663,247 | B2* | 3/2014 | Menn | A61B 17/122 606/142 |
| 8,974,371 | B2* | 3/2015 | Durgin | A61B 17/1285 600/104 |
| 9,005,219 | B2* | 4/2015 | Cohen | A61B 17/1285 606/142 |
| 9,980,725 | B2* | 5/2018 | Durgin | A61B 17/1285 |
| 10,143,479 | B2* | 12/2018 | Adams | A61B 17/122 |
| 10,154,842 | B2* | 12/2018 | Wells | A61B 17/10 |
| 10,201,339 | B2* | 2/2019 | Raybin | A61B 17/122 |
| 10,307,202 | B2* | 6/2019 | Smith | A61B 18/1206 |
| 10,335,159 | B2* | 7/2019 | Naveed | A61B 17/0057 |
| 10,575,857 | B2* | 3/2020 | King | A61B 17/1285 |
| 10,610,237 | B2* | 4/2020 | Estevez | A61B 17/1222 |
| 2005/0107809 | A1 | 5/2005 | Litscher et al. | |
| 2008/0027467 | A1* | 1/2008 | Satake | A61B 17/1285 606/143 |
| 2008/0140089 | A1* | 6/2008 | Kogiso | A61B 17/1285 606/142 |
| 2011/0196390 | A1* | 8/2011 | Kogiso | A61B 17/1227 606/151 |
| 2012/0065647 | A1* | 3/2012 | Litscher | A61B 17/122 606/143 |
| 2013/0123807 | A1* | 5/2013 | Wells | A61B 17/083 606/142 |
| 2013/0226199 | A1* | 8/2013 | Harris | A61B 17/10 606/142 |
| 2014/0088616 | A1* | 3/2014 | Clerc | A61B 17/083 606/142 |
| 2015/0190136 | A1* | 7/2015 | Cohen | A61B 17/1227 606/143 |
| 2015/0282813 | A1* | 10/2015 | Litscher | A61B 17/1285 606/143 |
| 2016/0228108 | A1* | 8/2016 | Raybin | A61B 17/122 |
| 2017/0020531 | A1* | 1/2017 | Naveed | A61B 17/1285 |
| 2017/0156785 | A1* | 6/2017 | Smith | A61B 18/1206 |
| 2018/0049745 | A1* | 2/2018 | Randhawa | A61B 17/1222 |
| 2018/0098771 | A1* | 4/2018 | King | A61B 17/1227 |
| 2018/0116677 | A1* | 5/2018 | Estevez | A61B 17/1285 |
| 2018/0153552 | A1 | 6/2018 | King et al. | |

FOREIGN PATENT DOCUMENTS

| | | |
|---|---|---|
| WO | 2011/022246 | 2/2011 |
| WO | 2017/095626 | 6/2017 |

* cited by examiner

RELOADABLE AND ROTATABLE CLIP

PRIORITY CLAIM

The present disclosure claims priority to U.S. Provisional Patent Application Ser. No. 62/564,805 filed Sep. 28, 2017; the disclosure of which is incorporated herewith by reference.

BACKGROUND

Pathologies of the gastrointestinal (GI) system, the biliary tree, the vascular system, and other body lumens and hollow organs are often treated through endoscopic procedures, many of which require hemostasis to control internal bleeding. Hemostasis clips grasp tissue surrounding a wound and hold edges of the wound together temporarily to allow natural healing processes to permanently close the wound. Specialized endoscopic clipping devices are used to deliver the clips to desired locations within the body after which the clip delivery device is withdrawn, leaving the clip within the body.

SUMMARY

The present disclosure relates to a system for treating tissue, comprising a clip assembly comprising a pair of clip arms, proximal ends of the clip arms engaging a distal portion of a central member slidably received within a channel of a capsule to be moved between an open configuration and a closed configuration, the clip arms biased toward the open configuration in which distal ends of the clip arms are separated from one another, the central member including the distal portion and a proximal portion connected to one another via a releasable connection which releases when subject to a force exceeding a predetermined threshold level, and an applicator configured to be releasably coupled to the clip assembly to move the clip assembly between the open and closed configurations, the applicator including an outer sleeve through which a control member extends, a distal end of the control member configured to engage a cavity of the proximal portion of the central member to move the central member relative to the capsule, a lumen of the outer sleeve sized and shaped to slidably receive the capsule therein.

In an embodiment, the applicator may further comprise an inner sleeve housed within the lumen of the outer sleeve at a proximal end of the outer sleeve to prevent the capsule from being moved proximally therepast.

In an embodiment, the capsule may include a pin extending laterally outward from an exterior surface thereof and the outer sleeve may include a longitudinal slot extending along a portion of a length thereof, proximally from a distal end of the outer sleeve, the longitudinal slot sized and shaped to receive the pin therein to prevent rotation of the capsule relative to the outer sleeve.

In an embodiment, the distal end of the control member may include an enlarged end configured to be received within a correspondingly sized and shaped cavity of the proximal portion of the central member.

In an embodiment, the enlarged end of the control member may be substantially cone-shaped tapering from a proximal end to a distal end thereof so that the enlarged end is longitudinally slidably insertable into the cavity.

In an embodiment, the cavity may be defined via a pair of deflectable alms biased toward a first configuration, in which a proximal opening of the cavity is smaller than a diameter of the proximal end of the enlarged end, and deflectable toward a second configuration in which the deflectable arms are moved away from one another to permit the enlarged end to be moved distally past the proximal opening into the cavity.

In an embodiment, the proximal portion may include a longitudinal slot extending proximally from the cavity to accommodate a length of the control member when the enlarged end is received within the cavity, the longitudinal slot and the cavity open to an exterior of the core member via a lateral opening through which the cavity receives the distal end of the control member.

In an embodiment, the cavity of the proximal portion may include a lateral opening via which the distal end is engagable with the cavity.

In an embodiment, the control member may include a hook-shaped distal end configured to engage the proximal portion.

In an embodiment, the applicator may include a handle portion including a handle shaft connected to the outer sheath via a flexible member and a spool slidably mounted over the handle shaft, the spool connected to a proximal end of the control member.

In an embodiment, the handle portion may further include an actuator coupled to the flexible member so that rotation of the actuator rotates the flexible member.

In an embodiment, the handle portion may further include an actuator coupled to the control member so that rotation of the actuator rotates the control member.

In an embodiment, the handle portion may include a stop element positioned along the handle shaft and biased in a first outward configuration to prevent the spool from being moved distally therepast, the stop element movable to a second inward configuration to permit the spool to be moved distally therepast.

In an embodiment, a proximal end of the capsule includes a longitudinal slot extending therein via which the distal end of the control member is engagable with the central member from a side thereof.

The present disclosure also relates to a reloadable clipping device, comprising a clip assembly comprising a pair of clip arms, proximal ends of the clip arms engaging a distal portion of a central member slidably received within a channel of a capsule to be moved between an open configuration and a closed configuration, the clip aims biased toward the open configuration in which distal ends of the clip arms are separated from one another, the central member including the distal portion and a proximal portion connected to one another via a releasable connection which releases when subject to a force exceeding a predetermined threshold level, the capsule including a pin extending laterally from an exterior surface thereof, and an applicator configured to be releasably coupled to the clip assembly to move the clip assembly between the open and closed configurations, the applicator including an outer sleeve through which a control member extends, a distal end of the control member configured to engage a cavity of the proximal portion of the central member to move the central member relative to the capsule, the outer sleeve including a longitudinal slot extending from a distal end of the outer sheath to a proximal end, the longitudinal slot sized and shaped to slidably receive the pin of the capsule therein to prevent a relative rotation between the capsule and the outer sheath.

The present disclosure also relates to a method for treating a tissue, comprising loading a clip assembly onto a distal portion of an applicator by engaging a distal end of a control member of the applicator into a proximal portion of a central member of the clip assembly, a distal portion of the clip assembly coupled to a proximal portion of clip arms and receiving a capsule of the clip assembly, in which the central member is slidably housed, in a channel of an outer sheath of the applicator through which the control member extends, inserting the clip assembly to a target site within a living body in a closed configuration in which clip arms are drawn into the capsule so that distal ends of the clip arms are constrained toward one another, moving the clip assembly toward the open configuration by moving the control wire and thereby the clip arms distally out of the capsule so that distal ends of the clip arms are separated from one another, rotating the clip assembly to a desired configuration relative to a target tissue at the target site, clipping the target tissue by moving the clip assembly toward the closed configuration over the target tissue and locking the clip assembly in the closed configuration.

BRIEF DISCLOSURE

DETAILED DESCRIPTION

The present disclosure may be further understood with reference to the following description and the appended drawings, wherein like elements are referred to with the same reference numerals. The present disclosure relates to a clipping system and, in particular, relates to a reloadable endoscopic clipping system. Exemplary embodiments of the present disclosure describe a clip assembly that may be loaded onto a distal end of an applicator assembly prior to an endoscopic procedure. Once a clip has been deployed at a desired target area in the body, the applicator assembly may be reloaded with a new clip. In particular, the applicator assembly is configured to connect to the clip assembly in a manner that permits rotation of the clip assembly. In other words, the clip assembly is permitted to rotate about a longitudinal axis thereof to position clip arms thereof in a desired configuration with respect to a target tissue to be clipped. It should be noted that the terms "proximal" and "distal," as used herein, are intended to refer to a direction toward (proximal) and away from (distal) a user of the device.

As shown in FIGS. 1-8, a system 100 according to an exemplary embodiment of the present disclosure comprises a clip assembly 102 that may be loaded on a distal portion of an applicator 104 prior to insertion of the system 100 into a living body for the clipping of target tissue. The applicator 104 is configured such that, after deployment of the clip assembly 102 in the living body, a new clip assembly 102 may be loaded onto the applicator 104 so that the same applicator 104 may be used to deliver a new clip assembly 102 to a second portion of target tissue in the living body. The clip assembly 102 includes a pair of clip arms 106 slidably movable within a capsule 108 to be moved between an open, tissue-receiving configuration and a closed, tissue-gripping configuration. The applicator 104 of this embodiment includes an outer sheath 110 at a distal end 114 of a flexible member 112 for slidably receiving the capsule 108 of the clip assembly 102 therein. In particular, the outer sheath 110 includes a longitudinal slot 116 extending along a length thereof from a distal end 118 of the outer sheath 110 to a proximal end 120, the longitudinal slot 116 sized to receive a pin 122 extending laterally from an exterior surface 124 of the capsule 108 to prevent rotation of the capsule 108, and thereby the clip assembly 102, relative to the outer sheath 110 about a longitudinal axis thereof. Since the clip assembly 102 is prevented from rotating relative to the outer sheath 110, rotation of the flexible member 112 via an actuator 126 of the applicator 104 rotates the outer sheath 110 and the clip assembly 102 about the longitudinal axis to position the clip aims 106 in a desired configuration relative to the target tissue. Features of the clip assembly 102 and the applicator 104 facilitating a releasable connection therebetween will be described in further detail below.

Figure 1:
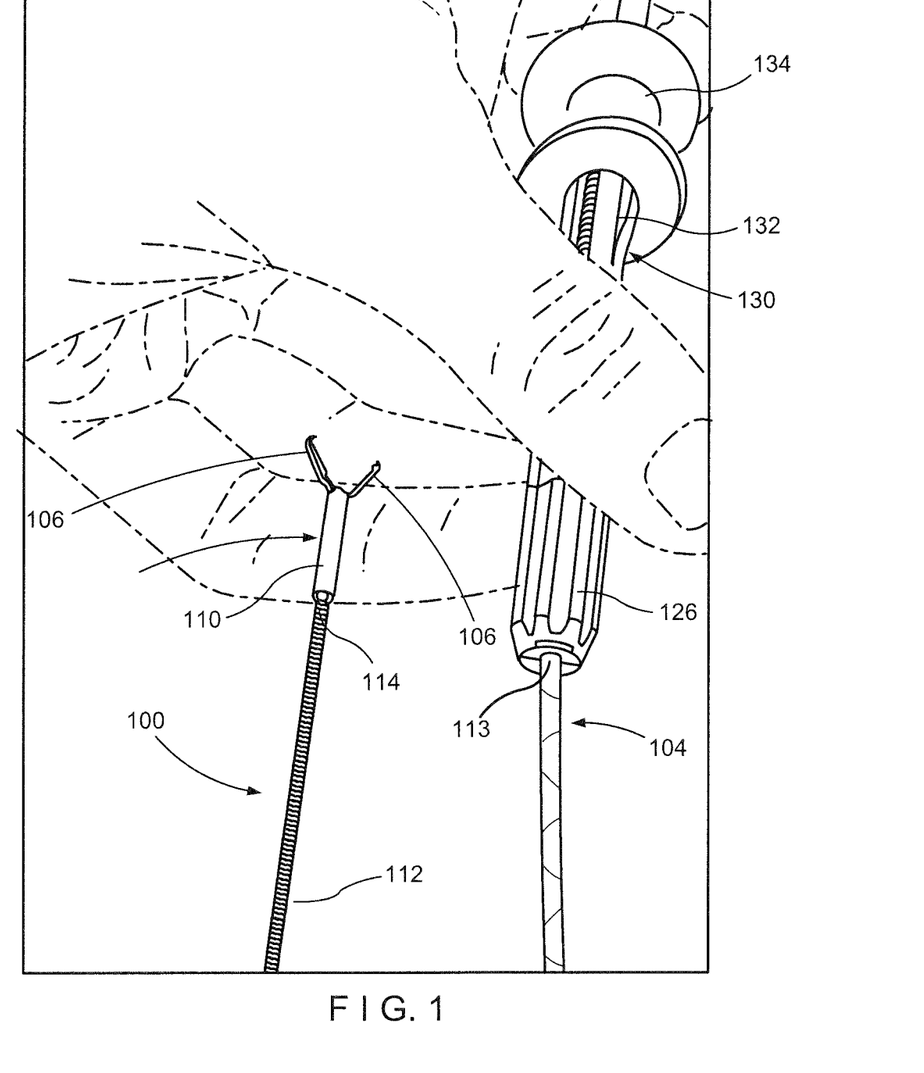
FIG. 1 shows a perspective view of a system according to an exemplary embodiment of the present disclosure.

The applicator 104 includes the outer sheath 110 and a control member 128 extending therethrough. The outer sheath 110 is connected to the distal end 114 of the flexible member 112, which connects the outer sheath 110 to a handle portion 130 at a proximal end 113 thereof. The flexible member may be formed, for example, as a coil of wire through which the control member 128 extends. As would be understood by those of skill in the art, the coil of wire preferably has sufficient flexibility to be passed through even tortuous paths of the living body and, in this embodiment, is sized and shaped to permit it to be passed through a working channel of a flexible endoscope or other insertion device. Although the flexible member is shown and described as a coil of wire, any other suitable flexible structure may be employed so long as the flexible member is capable of providing a force in compression sufficient to counter the tension to be places on the control member 108 from the clip assembly 102.

Figure 2:
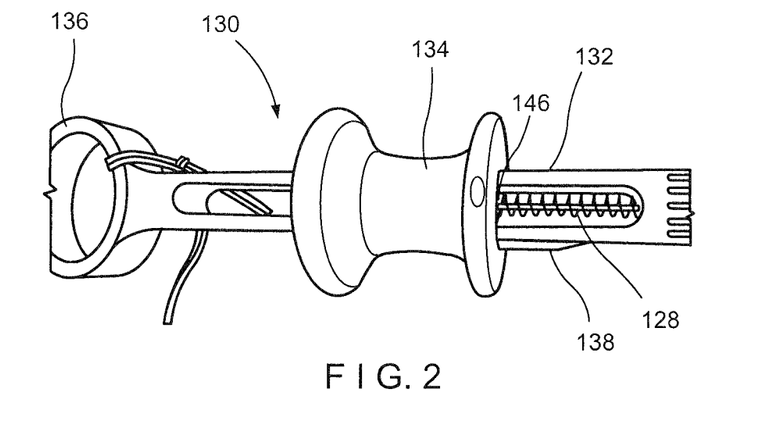
FIG. 2 shows a side view of a handle portion of an applicator of the system of FIG. 1.

As shown in FIGS. 1-2, the handle portion 130 at the proximal end 113 of the flexible member 112 includes a handle shaft 132 and a spool 134 slidably mounted thereover. The handle shaft 132 is rotatably connected to the proximal end 113 of the flexible member 112 so that rotation of the actuator 126, which is connected to the flexible member 112 proximally of the handle shaft 132, may rotate the flexible member 112 about the longitudinal axis, relative to the handle shaft 132. The spool 134 is connected to a proximal end 146 of the control member 128 so that moving the spool 134 distally and proximally with respect to the handle shaft 132 moves the control member 128 and thereby the clip arms 106 to which it is connected, between the open and closed configurations, respectively. The handle shaft 132 may include a thumb ring 136 at a proximal end thereof and a stop element 138 which, in a biased locking configuration extends laterally outward to prevent the spool 134 from being moved distally therepast. When it is desired to move the spool 134 beyond the stop element 138, however, a user of the system 100 may press the stop element 138 toward an unlocked configuration so that the spool 134 may be moved distally therebeyond. As will be described in further detail below, the spool 134 may be moved distally beyond the stop element 138 when it is desired to deploy the clip assembly 102 in the living body.

Figure 3:
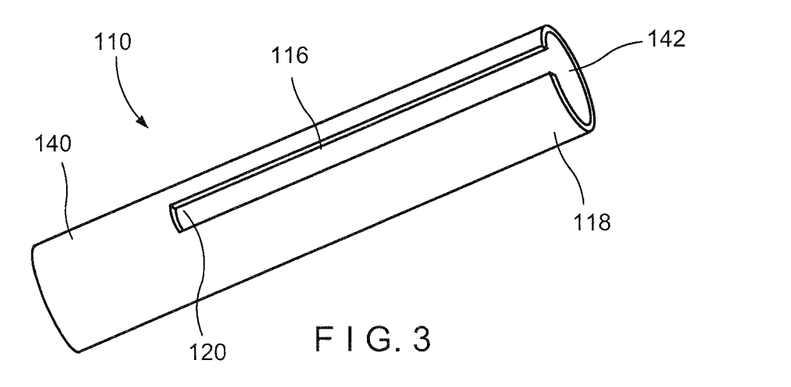
FIG. 3 shows a perspective view of an outer sheath of the applicator of the system of FIG. 1.

The outer sheath 110, as shown in FIG. 3, extends from a proximal end 140 fixed to the distal end 114 of the flexible member 112 to the distal end 118, and includes a channel 142 extending longitudinally therethrough. The channel 142 is sized and shaped to slidably receive the capsule 108 of the clip assembly 102 therein. The longitudinal slot 116 extends along a length of the outer sheath 110 proximally from the distal end 118 of the outer sheath 110 to the proximal end 120 and is sized and shaped to receive the laterally extending pin 122 of the capsule 108 therein so that the capsule 108 may be longitudinally slidable relative to the outer sheath 110 (i.e., along the longitudinal axis of the outer sheath 110) but is prevented from rotating relative to the outer sheath 110 (i.e., about the longitudinal axis of the outer sheath 110).

Figure 4:
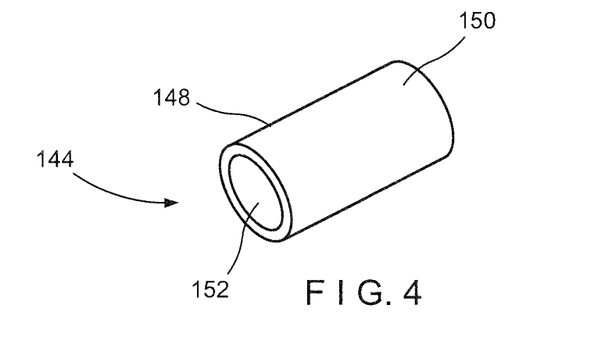
FIG. 4 shows a perspective view of an inner sheath of the applicator of the system of FIG. 1.

The applicator 104 may further include an inner sheath 144, as shown in FIG. 4, is fixed to the distal end 114 of the flexible member 112 within the outer sheath 110 at the proximal end 140 of the outer sheath 110. The inner sheath 144 is positioned within the outer sheath 110 to prevent the capsule 108 of the clip assembly 102 from acting as a stop for the clip assembly 102 by preventing the capsule 108 from being moved any further proximally within the outer sheath 110, as will be described in further detail below. The inner sheath 144 extends from a proximal end 148 connected to the distal end 114 of the flexible member 112 to a distal end 150, which is proximal of the distal end 118 of the outer sheath 110 so that the capsule 108 may be substantially received within the outer sheath 110. The inner sheath 144 includes a channel 152 extending therethrough so that the control member 128 extends through the flexible member 112, outer sheath 110 and the inner sheath 144 from the proximal end 136 connected to the spool 134 to an enlarged distal end 154 sized and shaped to be coupled to the clip arms 106. As will be described in further detail below, the control member 128 is longitudinally movable relative to the outer sheath 110, and thereby the capsule 108 received therewithin, to move the clip arms 106 between the open and closed configurations. Although the exemplary embodiment describes and shows the applicator 104 as including the inner sheath 144, it will be understood by those of skill in the art that the inner sheath 144 is not a required element of the applicator 104, as the applicator 104 is capable of functioning without it. The inner sheath 144, however, reduces the stress on the pin 122 when the capsule 108 is moved proximally with respect to the outer sheath 110.

Figure 5:
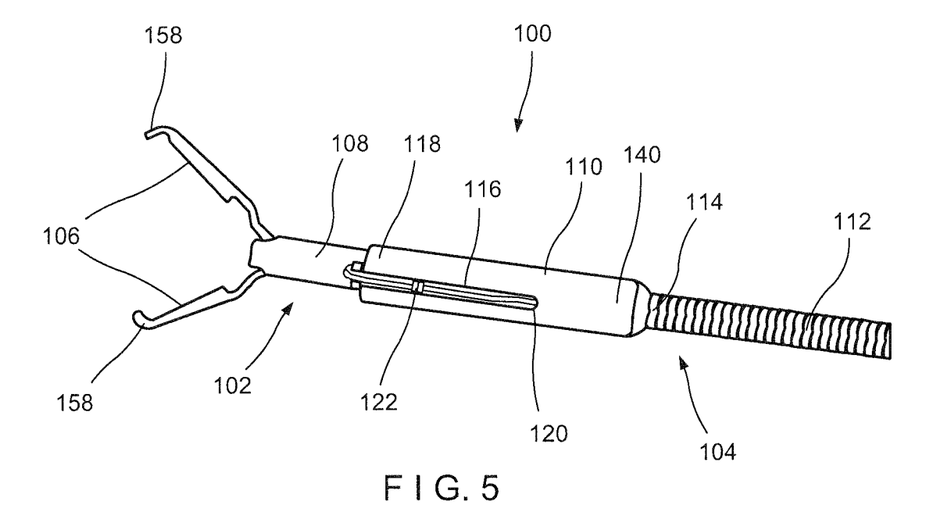
FIG. 5 shows a side view of a distal portion of the system of FIG. 1, including a clip assembly loaded onto the applicator.

As shown in FIG. 5, the clip assembly 102 includes the clip arms 106, proximal ends of which are, in this embodiment, connected to one another via a central member 156 that is slidably received within the capsule 108. This clip arms 106 in this embodiment are biased so that distal ends 158 thereof move apart from one another into the open, tissue-receiving configuration when no drawn into the capsule 108. When drawn into the capsule 108, the capsule 108 constrains the clip arms 106, holding the distal ends 158 thereof toward one another in the closed, tissue-gripping configuration. The central member 156 is longitudinally slidable within the capsule 108 to move the clip arms 106 between the open and closed configurations.

Figure 6:
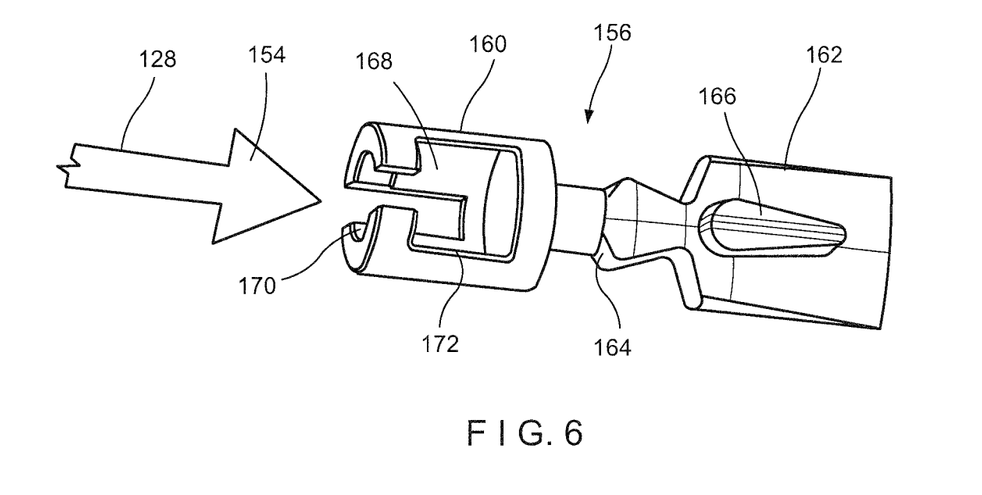
FIG. 6 shows a perspective view of a central member of the clip assembly of FIG. 1.

The central member 156, as shown in FIG. 6, includes a proximal portion 160 and a distal portion 162 connected to one another via a releasable connection 164 that is configured to release when subject to a force exceeding a predetermined threshold value. In one embodiment, the releasable connection 164 may be a frangible link such as, for example, a welding, a decreased diameter portion, or adhesive that breaks or otherwise uncouples when a sufficient force is exerted thereon. The distal portion 162 engages a proximal portion of the clip arms 106 via a pair of protrusions 166 extending therefrom and received within a pair of correspondingly sized and shaped openings extending through proximal portions of the clip arms 106. The protrusions 166 are configured to hold the pair of arms 106 in position relative to one another.

The proximal portion 160 is configured to engage the enlarged distal end 154 of the control member 128. The proximal portion 160 includes a cavity 168 sized and shaped to receive the enlarged distal end 154 of the control member 128 and open to an exterior thereof via a proximal opening 170. The proximal opening 170 is sized and shaped to receive a portion of the control member 128 extending proximally from the enlarged distal end 154. A cross-sectional area of the proximal opening 170 is smaller than a cross-sectional area of the cavity 168 so that, once the enlarged distal end 154 is received within the cavity 168, the enlarged distal end 154 is prevented from being disengaged therefrom via a proximal force on the control member 128.

The proximal portion 160 may be configured to engage the distal portion 154 of the control member 128 in any of a variety of ways so long as the control member 128 is coupled to the central member 156 in a way that permits movement of the control member 128 to control movement of the central member 156, and thereby the clip arms 106, relative to the capsule 108 in which it is received. In one embodiment, the cavity 168 and proximal opening 170 may be defined via opposed arms 172 which may be spreadable as the enlarged distal end 154 is pressed distally thereagainst to permit the enlarged distal end 154 to be moved distally past the proximal opening 170 and into the cavity 168. The opposed arms 172 in this embodiment are biased so that once the enlarged distal end 154 is received within the cavity 168, the opposed arms 172 revert to their initial configuration, locking the enlarged distal end 154 within the cavity 168. A conically shaped enlarged distal end 154, which tapers toward a distal end, may be particularly suitable for the cavity 168 and proximal opening 170 described above. It will be understood by those of skill in the art, however, that the enlarged distal end 154 may have any of a number of shapes so long as the enlarged distal end 154 may be sized and shaped to be received and held within the cavity 168. In another example, the enlarged distal end 154 may be ball-shaped.

According to a further embodiment, the proximal portion 160 may also include a lateral opening 186 which opens the cavity 168 and proximal opening 170 to an exterior of the central member 156. In this embodiment, a user may choose to couple the control member 128 to the proximal portion from a side of the central member 156 via the lateral opening 186 so that the enlarged distal end 154 is received within the cavity 168 and a proximally extending portion of the control member 128 is received within the proximal opening 170. Upon insertion of the enlarged distal end 154 into the cavity 168, the capsule 108 may be moved proximally thereover, covering the lateral opening 186 and preventing the enlarged distal end 154 from being disengaged therefrom.

Figure 7:
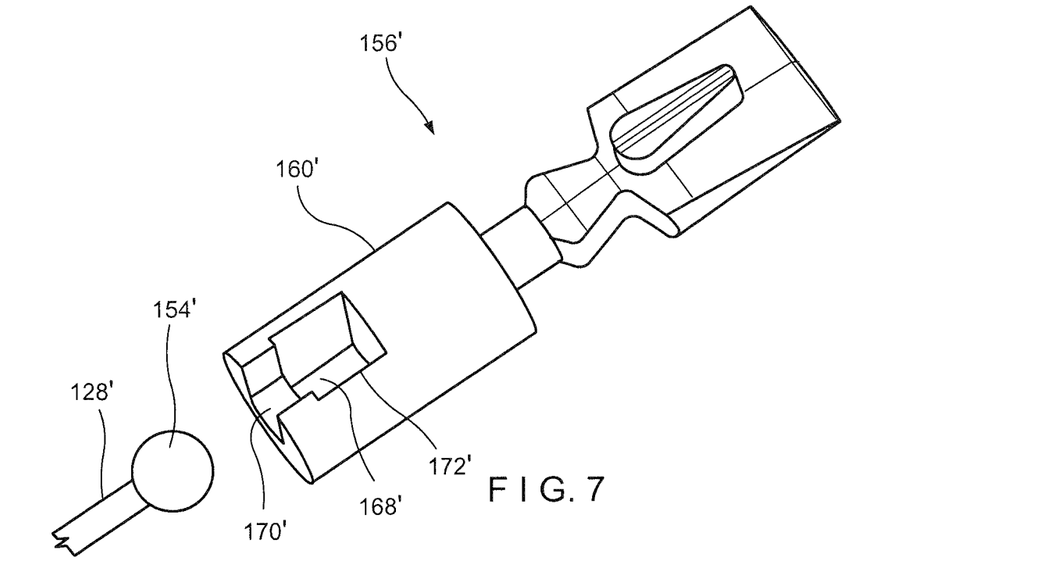
FIG. 7 shows a perspective view of a central member of a clip assembly according to an alternate embodiment of the system of FIG. 1.

In another embodiment, as shown in FIG. 7, a central member 156' may be substantially similar to the central member 156 described above. A proximal portion 160' of the central member 156', however, only permits insertion of an enlarged distal end 154' of a control member 128' into a cavity 168' via a lateral opening 186' so that the enlarged distal end 154' must be inserted from a side of the central member 156'. Similarly to the proximal portion 160', a portion of the control member 128' extending proximally from the enlarged distal end 154' is received within a proximal opening 170', which has a smaller cross-sectional area than the cavity 168' to prevent the control member 128' from being disengaged therefrom via a proximal force thereon. A ball-shaped enlarged distal end 154' may be particularly suited for this embodiment, but may have any of a variety of shapes and configurations.

Figure 8:
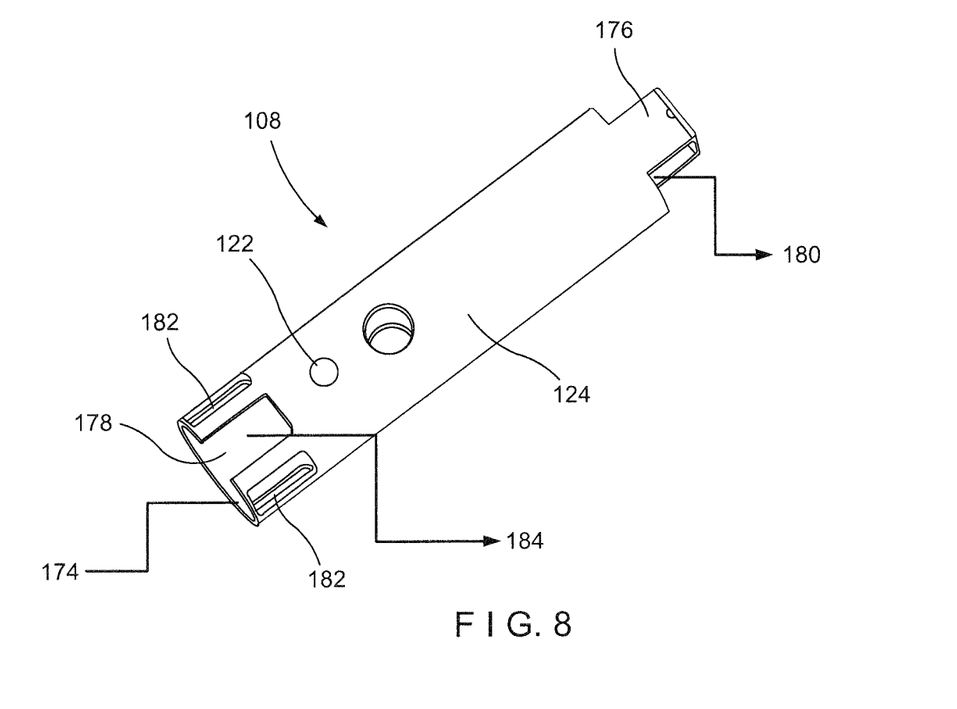
FIG. 8 shows a perspective view of a capsule of the clip assembly of FIG. 1.

As shown in FIG. 8, the capsule 108 extends from a proximal end 174 to a distal end 176 and includes a channel 178 extending longitudinally therethrough. The channel 178 is sized and shaped to slidably receive the central member 156 and at least a proximal portion of the clip arms 106 therein. The distal end 176 may include a pair of cut outs 180 sized and shaped to receive the pair of arms 106 therein. The capsule 108 may also include a pair of locking windows 182 extending laterally therethrough for engaging corresponding locking tabs of the arms 106. As will be described in further detail below, when the locking tabs are received within the locking windows 182, the clip arms 106 are locked within the capsule 108 in the closed configuration. The locking windows 182 may be positioned proximate the proximal end 174 so that the arms 106 may be repeatedly moved between the open and the closed configurations until it is desired to lock the clip assembly 102 in the closed configuration.

The capsule 108 also includes the pin 122 extending laterally from the exterior surface 124 of the capsule 108 to be slidably received within the longitudinal slot 116 of the outer sheath 110 of the applicator 104 during loading of the clip assembly 102 onto the applicator 104. The pin 122 prevents rotation of the clip assembly 102 relative to the outer sheath 110 about the longitudinal axis thereof, so that clip assembly 102 may be rotated via a rotation of the flexible member 112.

The clip arms 106 according to this embodiment are biased toward the open configuration and may be shaped so that, when the clip assembly 102 is coupled to the applicator 104, release of the control wire 128 and/or a slight distal force thereon, causes the clip arms 106 to be moved distally with respect to the capsule 108. In particular, the clip arms 106 may include a curve extending therealong. This curve, along with the elastic nature of the arms 106, moves the clip arms 106 distally relative to the capsule 108 toward the open configuration, unless a force is exerted thereon. In other words, once the clip arms 106 are constrained toward the closed configuration via a proximal force exerted on the control wire 128, the clip arms 106 may only remain in the closed configuration if there is a high enough axial load—i.e., the user holds the clip arms 106 in the closed configuration via use of the handle portion 130. Thus, according to this embodiment, when the user releases the spool 134 of the handle portion 130, the clip arms 106 are configured to revert toward their biased configuration by sliding with respect to the capsule 108 toward the open configuration.

As described above, the proximal ends of the arms 106 may also include locking tabs extending laterally outward therefrom. The locking tabs of each of the arms 106 extend away from one another toward an interior of the capsule 108. The proximal ends of the arms 106 are also biased away from one another so that the locking tabs slide along the interior of the capsule 108 as the central member 156 is moved longitudinally relative to the capsule 108. Once it is desired to lock the clip assembly in the closed configuration, however, the user may draw the central member 156 proximally until the locking tabs are received within the locking windows 182 and the proximal ends of the arms 106 are permitted to revert to their biased configuration so that the locking tabs engage the locking windows 180.

Prior to being loaded on the applicator 104, the clip assembly 102 may be stored, for example, in a cartridge configured to facilitate loading of the clip assembly 102 in the applicator 104. The cartridge defines a space therein sized and shaped to house the clip assembly 102. The clip assembly 102 may be housed within the cartridge, in the assembled configuration, with the proximal portion 160 of the central member 156 extending proximally of the proximal end 174 of the capsule 108 so that the enlarged distal end 154 of the control member 128 may be engaged with the proximal portion 160 of the central member 156. Alternatively, where it is desired to couple the control member 128 to the central member 156 from a side thereof via, for example, the lateral opening 186, the capsule 108 may include a longitudinal slot 184 at the proximal end 174 via which the enlarged end 154 may engage the proximal portion 160 so that the proximal portion 160 is not required to extend proximally of the proximal end 174 of the capsule 108.

An exemplary method for loading the clip assembly 102 to the applicator 104 comprises inserting the outer sheath 110 and the distal end 154 of the control member 128 into the cartridge, with the control member 128 distally extended so that the enlarged distal end 154 is positioned distally of the distal end 118 of the outer sheath 110. In one embodiment, the enlarged distal end 154 may be pushed distally against the proximal portion 160 of the central member 156, causing opposed arms 172 to spread apart to permit the enlarged distal end 154 to be moved distally past the proximal opening 170 and into the cavity 168. Once the enlarged distal end 154 has been received within the cavity 168, the opposed arms 172 revert to their biased configuration, holding the enlarged distal end 168 within the cavity 168. In another embodiment, the enlarged distal end 154 may be inserted into the cavity 168 via the lateral opening 186 from a side of the central member 156. It will be understood by those of skill in the art that the clip assembly 102 may be housed in the cartridge in either the open or closed configuration, depending on a desired manner of engagement of the applicator 104 with the clip assembly 102.

Once the control member 128 is engaged with the central member 156, the outer sheath 110 is moved distally relative to the control wire 128 and the clip assembly 102 to which it is connected so that the outer sheath 110 is slid distally over the capsule 108. The outer sheath 110 may be moved distally over the capsule 108 so that the pin 122 is slidingly received within the longitudinal slot 116 of the outer sheath 110. Once the proximal end 174 of the capsule 108 abuts the distal end 150 if the inner sheath 144 and/or the pin 122 abuts the proximal end 120 of the longitudinal slot 116, the outer sheath 110 cannot be moved further distally relative to the capsule 108 so that, if necessary, the control member 128 may be drawn proximally relative to the outer sheath 110 to move the clip assembly 102 toward the closed configuration.

In the closed configuration, the clip assembly 102, which is loaded onto the applicator 104, may be drawn out of the applicator 104.

In use, after the clip assembly 102 has been loaded onto the applicator 104, the clip assembly 102 is inserted through a working channel of an endoscope (or any other insertion device) and inserted into the body (e.g., through a natural body lumen) to a site adjacent to a target portion of tissue to be clipped. The clip assembly 102 is inserted into the body in the closed configuration and positioned adjacent to the target tissue. The clip assembly 102 may be rotated, as desired, for optimal clipping of the target tissue, by rotating the flexible member 112 via the actuator 126. Since, as described above, the capsule 108 is prevented from rotating relative the outer sheath 110, rotation of the flexible member 112 correspondingly results in rotation of the clip assembly 102. The control member 128 may be moved distally relative to the outer sheath 110 via the spool 134 to move the clip assembly 102 toward the open configuration. As described above, the clip arms 106 may be shaped (e.g., curved) in a way so that release of the spool 134 and/or a slight distal force exerted on the spool 134 draws the clip arms 106 distally out of the capsule 108 toward the open configuration. This distal force may cause the capsule 108 to be moved slight distally with respect to the outer sheath 110, but will not be sufficient to cause the capsule 108 to be entirely disengaged from the outer sheath 110. Furthermore, the stop element 138, which prevents the spool 134 from being moved distally therebeyond, defines a maximum extension of the control member 128 relative to the outer sheath 110, which prevents the clip arms 106, and thereby the capsule 108, from being moved far enough distally relative to the outer sheath 110 to become disengaged therefrom.

The clip assembly 102 may be moved between the open and closed configurations by moving the control member 128 distally and proximally, respectively, relative to the outer sheath 110, until the target tissue is gripped between the clip arms 106, as desired. The clip assembly 102 may then be locked in the closed configuration by drawing the control member 128 further proximally relative to the outer sheath 110. As described above, the capsule 108 abutting the inner sheath 144 and/or the pin 122 engaging the proximal end 120 of the longitudinal slot 116 prevents the capsule 108 from being moved any further proximally relative to the outer sheath 110. Thus, continued proximal motion of the control wire 128 causes the clip arms 106 to be drawn further proximally into the capsule 108 until the locking tabs at the proximal ends of the clip arms 106 engage the locking windows 182. As described above, the proximal ends of the clip arms 106 are biased outward so that once the proximal ends are received within the locking windows 182, the proximal ends revert to their biased outward configuration causing the locking tabs to engage the locking windows and locking the clip assembly in the closed configuration. In this locked configuration, the clip arms 106 are prevented from moving relative to the capsule 108 so that even further proximal motion of the control member 128 relative to the outer sheath 110 causes the releasable connection 164 of the central member 156 to disconnect the proximal and distal portions 160, 162 from one another. The release of the releasable connection 164 may be detected by the user via a tactile feedback so that once the releasable connection 164 is released or uncoupled, the user may move the control wire 128 distally relative to the outer sheath 110 to use the separated proximal portion 160 to push the distal portion 162 of the central member 156, and thereby the capsule 108 to which the arms 106 are locked, distally relative to the outer sheath 110. To deploy the clip assembly 102 in the body, the user may move the locking tab 38 toward the unlocked configuration so that the spool 134 may be moved distally therebeyond. Moving the spool 134 beyond the stop element 138 pushes the capsule 108 distally out of the sheath 110 so that drawing the applicator 104 proximally out of the body leaves the clip assembly 102 (minus the proximal portion 160 of the central member 156) in the body clipped over the target tissue. If desired, a new clip assembly 102 may be loaded onto the applicator 104, in the same manner as described above. However, a user must first remove the proximal portion 160 that remains coupled to the distal end of the control wire 128. After the new clip has been loaded, the device may be used to clip a second portion of tissue. This process may be repeated using the same applicator 104 as many times as needed or desired.

As shown in FIGS. 9-12, a system 200 according to another exemplary embodiment of the present disclosure may be substantially similar to the system 100, comprising a clip assembly 202 loadable onto a distal portion of an applicator 204 for insertion into a living body for the clipping of target tissue. The system 200, however, differs from the system 100 in that the clip assembly 202 is permitted to rotate about a longitudinal axis thereof via a rotation of a control member 228 connected thereto, rather than via the rotation of a flexible member 212 of the applicator 204.

Figure 10:
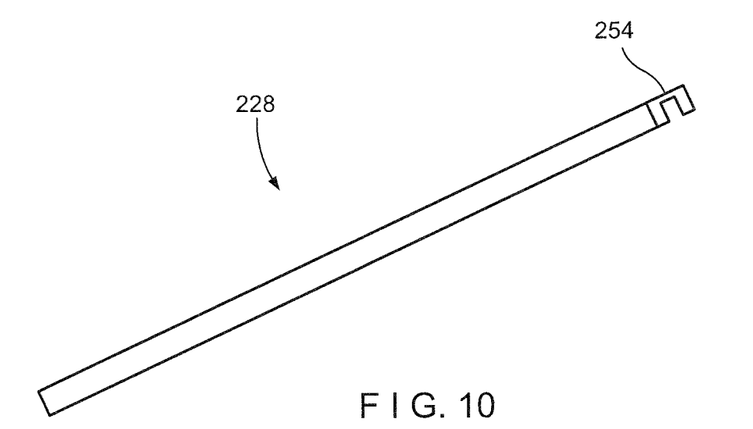
FIG. 10 shows a distal portion of a control member of an applicator according to the system of FIG. 9.

The applicator 204 may be substantially similar to the applicator 104, including an outer sheath 210, an inner sheath (not shown) and the control member 228 extending therethrough. The outer sheath 210, and the inner sheath mounted within a proximal end 240 of the outer sheath 210 are connected to a distal end 214 of a flexible member 212, which extends to a proximal end 213 connected to a handle portion 230. Rather than enlarged distal end, a distal end 254 of the control member 228 of this embodiment, as shown in FIG. 10, includes a hook or u-shaped bend so that engagement of the distal end 254 with the clip assembly 202 permits a rotation of the control member 228 about a longitudinal axis of system 200 to translate into a corresponding rotation of the clip assembly 202.

Figure 11:
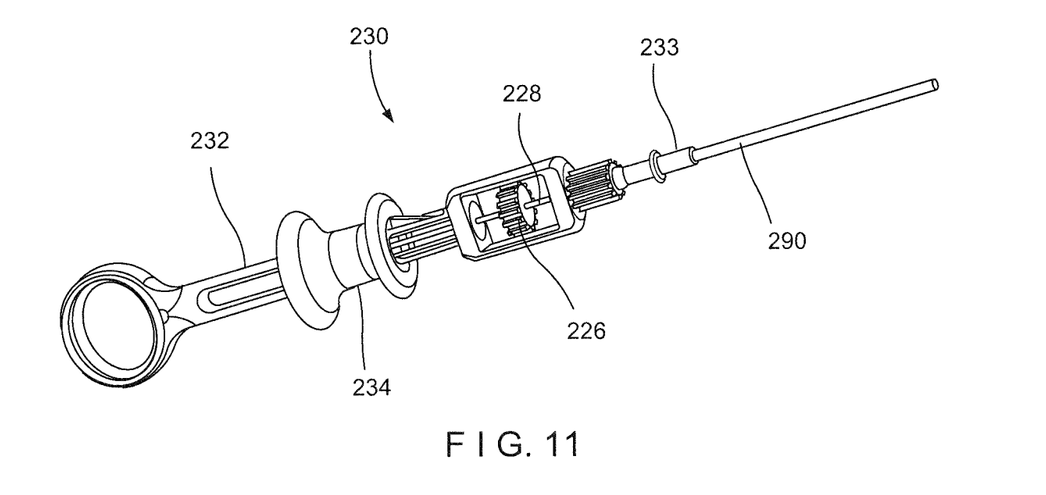
FIG. 11 shows a handle portion of the applicator of the system of FIG. 1.

As shown in FIG. 11, the handle portion 230 may be substantially similar to the handle portion 130, including a handle shaft 232 and a spool 234 slidably mounted thereover for moving the control wire 228 longitudinally relative to the outer sheath 210. An actuator 226 of the handle portion 230, however, is connected to the control wire 228 to provide a rotational force thereto. In this embodiment, the actuator 226 may, for example, may be configured as a thumb wheel, rotation of which rotates the control wire 228 and, consequently, a clip assembly 202 coupled thereto. The actuator 226 may be positioned along the handle shaft 232 distally of a distal-most position of the spool 234 so as not to interfere with the longitudinal motion of the spool 234 relative to the handle shaft 232. The handle portion 230 may also include a hypotube 290 extending distally from a distal end of 233 of the handle shaft 232 for providing a rigid support for the control wire 228 as it rotates.

Figure 9:
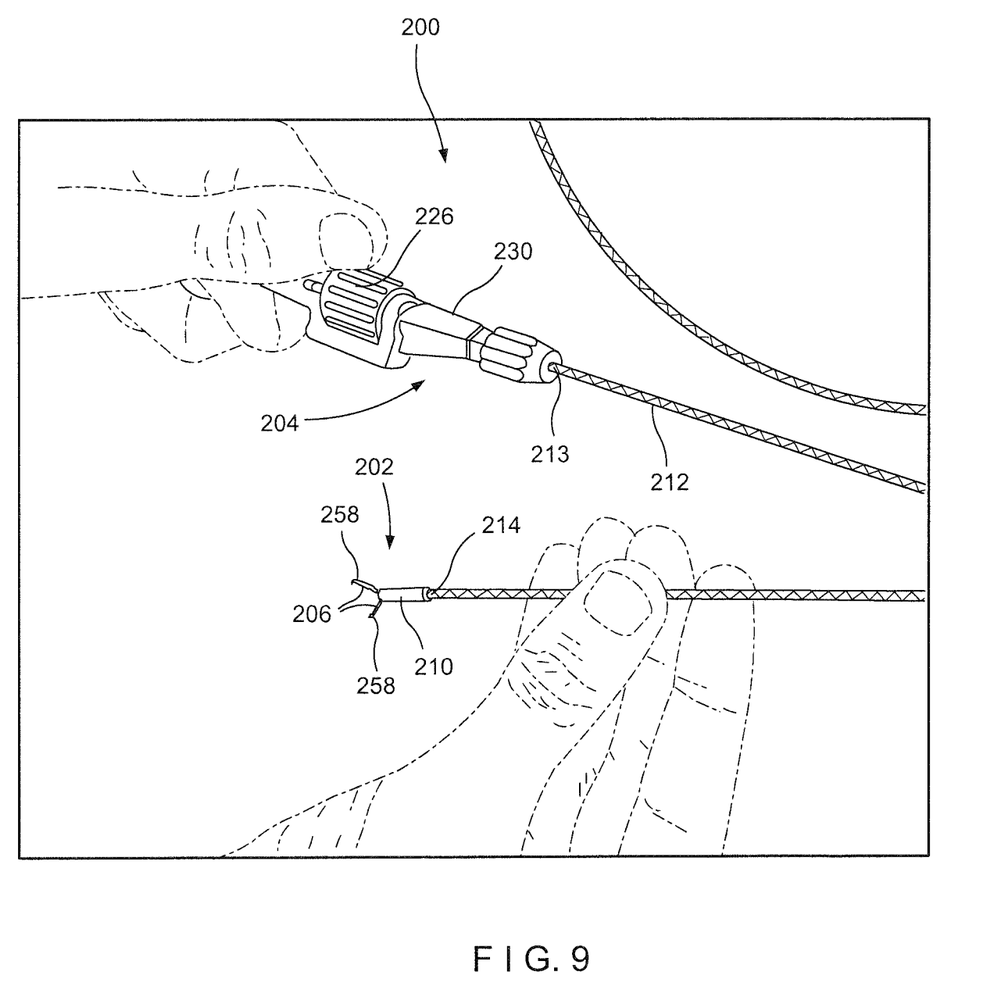
FIG. 9 shows a perspective view of a system according to another exemplary embodiment of the present disclosure.
Figure 12:
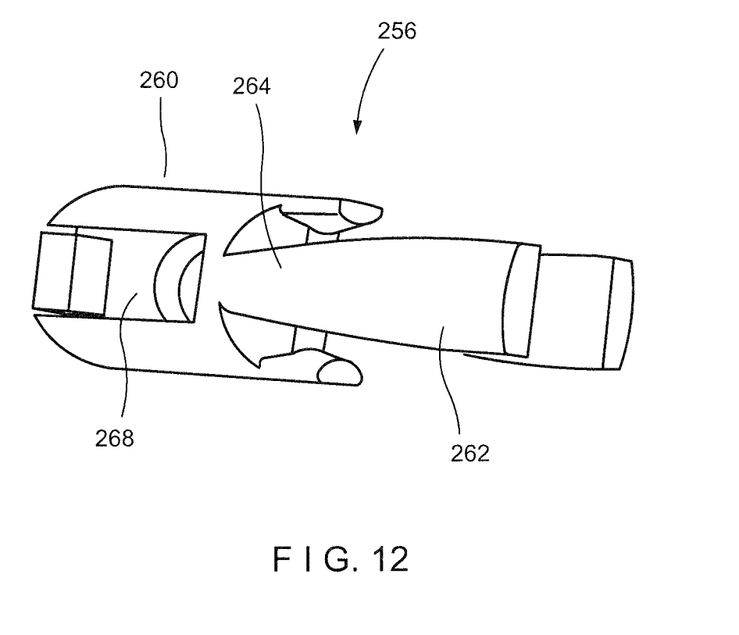
FIG. 12 shows a central member of a clip assembly according to the system of FIG. 9.

The clip assembly 202 is substantially similar to the clip assembly 102, comprising a pair of clip arms 206 slidably received within a capsule (not shown) via a central member 256 to be moved between an open, tissue-receiving configuration, in which distal ends 258 of the clip arms 206 are separated from one another to receive tissue therebetween, and a closed tissue-gripping configuration, in which distal ends 258 are drawn toward one another to grip tissue therebetween. Similarly to the central member 156, the central member 256 includes a proximal portion 260 configured to be coupled to the control member 228 of the applicator 204 and a distal portion 262 configured to be coupled to a proximal portion of the clip arms 206. The proximal and distal portions 260, 262 are connected to one another via a releasable connection such as, for example, a releasable connection 264 designed to release (e.g., break, uncouple) when subject to a force exceeding a predetermined threshold value. The proximal portion 260, however, includes a cavity 268, recess or other structure that is specifically sized and shaped to receive the hook-shaped distal end 254 of the control member 228. Engagement of the hook-shaped distal end 254 permits a rotation of the control member 228 to translate into a corresponding rotation of the central member 256, and thereby the clip arms 206, about the longitudinal axis of the clip assembly 202.

The clip assembly 202 may be loaded onto the applicator 204 in substantially the same manner as described above in regard to the system 100. In particular, the distal end 254 is engaged with the cavity 268 of the proximal portion 260 of the central member 256 from a side thereof. Once the clip assembly 202 has been loaded onto the applicator 204, the system 100 may be utilized in substantially the same manner as the system 100. Once at the target site, however, the clip assembly 202 may be rotated into a desired position via rotation of the thumb wheel 226. Clipping of the target tissue and deployment of the clip assembly 202 may be achieved in substantially the same manner as described above with respect to the system 100.

It will be apparent to those skilled in the art that various modifications may be made in the present disclosure, without departing from the scope of the disclosure.

What is claimed is:

1. A system for treating tissue, comprising:
a clip assembly comprising a pair of clip arms, proximal ends of the clip arms engaging a distal portion of a central member slidably received within a channel of a capsule to be moved between an open configuration and a closed configuration, the clip arms biased toward the open configuration in which distal ends of the clip arms are separated from one another, the central member including the distal portion and a proximal portion connected to one another via a releasable connection which releases when subject to a force exceeding a predetermined threshold level; and
an applicator configured to be releasably coupled to the clip assembly to move the clip assembly between the open and closed configurations, the applicator including an outer sleeve through which a control member extends, a distal end of the control member configured to engage a cavity of the proximal portion of the central member to move the central member relative to the capsule, a lumen of the outer sleeve sized and shaped to slidably receive and non-rotatably engage the capsule therein.

2. The system of claim 1, wherein the applicator further comprises an inner sleeve housed within the lumen of the outer sleeve at a proximal end of the outer sleeve to prevent the capsule from being moved proximally therepast.

3. The system of claim 1, wherein the capsule includes a pin extending laterally outward from an exterior surface thereof and the outer sleeve includes a longitudinal slot extending along a portion of a length thereof, proximally from a distal end of the outer sleeve, the longitudinal slot sized and shaped to receive the pin therein to prevent rotation of the capsule relative to the outer sleeve.

4. The system of claim 1, wherein the distal end of the control member includes an enlarged end sized and shaped to correspond to the cavity of the proximal portion of the central member.

5. The system of claim 4, wherein the enlarged end of the control member is substantially cone-shaped tapering from a proximal end to a distal end thereof so that the enlarged end is longitudinally slidably insertable into the cavity.

6. The system of claim 5, wherein the cavity is defined via a pair of deflectable arms biased toward a first configuration, in which a proximal opening of the cavity is smaller than a diameter of the proximal end of the enlarged end, and deflectable toward a second configuration in which the deflectable arms are moved away from one another to permit the enlarged end to be moved distally past the proximal opening into the cavity.

7. The system of claim 4, wherein the proximal portion includes a longitudinal slot extending proximally from the cavity to accommodate a length of the control member when the enlarged end is received within the cavity, the longitudinal slot and the cavity open to an exterior of the central member via a lateral opening through which the cavity receives the distal end of the control member.

8. The system of claim 1, wherein the cavity of the proximal portion includes a lateral opening via which the distal end is engagable with the cavity.

9. The system of claim 1, wherein the control member includes a hook-shaped distal end configured to engage the proximal portion.

10. The system of claim 1, wherein the applicator includes a handle portion including a handle shaft connected to the outer sleeve via a flexible member and a spool slidably mounted over the handle shaft, the spool connected to a proximal end of the control member.

11. The system of claim 10, wherein the handle portion further includes an actuator coupled to the flexible member so that rotation of the actuator rotates the flexible member.

12. The system of claim 10, wherein the handle portion further includes an actuator coupled to the control member so that rotation of the actuator rotates the control member.

13. The system of claim 10, wherein the handle portion includes a stop element positioned along the handle shaft and biased in a first outward configuration to prevent the spool from being moved distally therepast, the stop element movable to a second inward configuration to permit the spool to be moved distally therepast.

14. The system of claim 1, wherein a proximal end of the capsule includes a longitudinal slot extending therein via which the distal end of the control member is engagable with the central member from a side thereof.

15. A reloadable clipping device, comprising:
a clip assembly comprising a pair of clip arms, proximal ends of the clip arms engaging a distal portion of a central member slidably received within a channel of a capsule to be moved between an open configuration and a closed configuration, the clip arms biased toward the open configuration in which distal ends of the clip arms are separated from one another, the central member including the distal portion and a proximal portion connected to one another via a releasable connection which releases when subject to a force exceeding a predetermined threshold level, the capsule including a pin extending laterally from an exterior surface thereof; and
an applicator configured to be releasably coupled to the clip assembly to move the clip assembly between the open and closed configurations, the applicator including an outer sleeve through which a control member extends, a distal end of the control member configured to engage a cavity of the proximal portion of the central member to move the central member relative to the capsule, the outer sleeve including a longitudinal slot extending from a distal end of the outer sheath to a proximal end, the longitudinal slot sized and shaped to slidably receive the pin of the capsule therein to prevent a relative rotation between the capsule and the outer sheath.

16. A method for treating a tissue, comprising:

loading a clip assembly onto a distal portion of an applicator by engaging a distal end of a control member of the applicator into a proximal portion of a central member of the clip assembly, a distal portion of the central member coupled to a proximal portion of clip arms and receiving a capsule of the clip assembly, in which the central member is slidably housed, in a channel of an outer sheath of the applicator through which the control member extends so that the capsule is non-rotatably engaged to the outer sheath;

inserting the clip assembly to a target site within a living body in a closed configuration in which clip arms are drawn into the capsule so that distal ends of the clip arms are constrained toward one another;

moving the clip assembly toward the open configuration by moving the control wire and thereby the clip arms distally out of the capsule so that distal ends of the clip arms are separated from one another;

rotating the clip assembly to a desired configuration relative to a target tissue at the target site; and clipping the target tissue by moving the clip assembly toward the closed configuration over the target tissue and locking the clip assembly in the closed configuration.

17. The method of claim 16, wherein rotating the clip assembly includes rotating the control member about a longitudinal axis thereof.

18. The method of claim 17, wherein the outer sheath includes a longitudinal slot extending from a distal end of the outer sheath to a proximal end, the longitudinal slot sized and shaped to slidably receive a pin extending laterally outward from an exterior surface of the capsule to prevent relative rotation therebetween.

19. The method of claim 16, wherein rotating the clip assembly includes rotating a flexible member extending proximally from the outer sheath.

20. The method of claim 16, further comprising deploying the clip assembly in the body, clipped over the target tissue, by drawing the control member proximally until a releasable connection connecting the proximal and distal portions of the central member is released.

* * * * *